United States Patent [19]

Kijima et al.

[11] 4,039,573

[45] Aug. 2, 1977

[54] PROCESS FOR PREPARATION OF 1,4-BENZOHYDROQUINONE DERIVATIVES

[75] Inventors: Shizumasa Kijima; Isao Yamatsu, both of Tokyo; Kimio Hamamura, Kashiwa; Norio Minami, Kawasaki; Youji Yamagishi; Yuichi Inai, both of Tokyo, all of Japan

[73] Assignee: Eisai Co., Ltd., Tokyo, Japan

[21] Appl. No.: 621,084

[22] Filed: Oct. 9, 1975

[30] Foreign Application Priority Data

Oct. 11, 1974 Japan .................................. 49-116184

[51] Int. Cl.$^2$ ........................ C07C 43/22; C07C 69/16
[52] U.S. Cl. ............................ 260/479 R; 260/613 D
[58] Field of Search ..................... 260/479 R, 613 D

[56] References Cited

U.S. PATENT DOCUMENTS

| 3,118,914 | 1/1964 | Gloor et al. | 260/613 D |
| 3,349,113 | 10/1967 | Gloor et al. | 260/479 R |
| 3,670,031 | 6/1972 | Gloor et al. | 260/479 R |

*Primary Examiner*—Jane S. Myers
*Attorney, Agent, or Firm*—Blanchard, Flynn, Thiel, Boutell & Tanis

[57] ABSTRACT

2,3-dimethoxy-5-substituted-6-methyl-1,4-benzohydroquinone or 1-monoester thereof is prepared by reacting 2,3-dimethoxy-6-methyl-1,4-benzohydroquinone or 1-monoacylester thereof with prenol, isoprenol or derivatives thereof in the presence of an acidic catalyst for condensation which is adsorbed on an adsorbent. This obtained compound is easily converted to quinone compounds which produces many clinical effects in medical and pharmaceutical uses.

4 Claims, No Drawings

PROCESS FOR PREPARATION OF 1,4-BENZOHYDROQUINONE DERIVATIVES

BACKGROUND OF THE INVENTION

1. Field of the Invention

This invention relates to a process for producing 1,4-benzohydroquinone derivatives expressed by the following chemical formula (I):

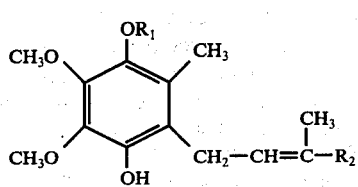

(where $R_1$ stands for hydrogen or an acyl group, and $R_2$ stands for the following formula:

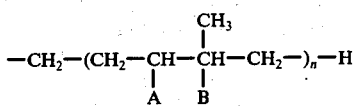

where $n$ is 0 or an integer of 1 to 11, and A and B stand for hydrogen or they may form valence bond to form a double bond between the two carbon atoms attached to A and B), that is, 2,3-dimethoxy-5-substituted 6-methyl-1,4-benzohydroquinone or monoester thereof.

1. Description of the Prior Art

The compounds (I) obtained according to the method of the present invention can be easily converted, if so desired, into quinone compounds expressed by the following chemical formula (II):

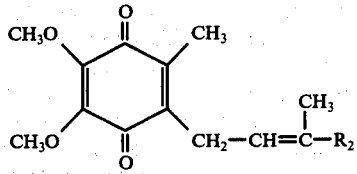

(where $R_2$ is defined above) by oxidizing the compound (I) through the process of hydrolysis. The compounds (II) are generally known as coenzyme Q, and of these compounds, the one in which A and B form valence bond to form a double bond and $n = 9$, that is, 2,3-dimethoxy-5-methyl-6-decaprenyl-1,4-benzoquinone [2,3-dimethoxy-5-methyl-6-(3′,7′,1-1′,15′,19′,23′,27′,31′,35′,39′-decamethyltetracontadic-aene-2′,6′,10′,14′,18′,22′,26′,30′,34′,38′-yl)-1,4-benzoquinone] is known as coenzyme $Q_{10}$. This substance has close relation to the electron transfer system in the organism and plays an important role for generation of energy, and it is expected to produce many clinical effects in medical and pharmaceutical uses. There are known several methods for synthesizing a series of quinone compounds represented by the said coenzyme $Q_{10}$. For instance, 2,3-dimethoxy-6-methyl-1,4-benzohydroquinone or 1-monoacylate thereof and (iso)decaprenol or its reactive derivative are reacted in the presence of an acid condensation catalyst such as for example a protonic acid such as formic acid, sulfuric acid, hydrochloric acid, phosphoric acid or p-toluenesulfonic acid, a Lewis acid such as zinc chloride, aluminum chloride or boron trifluoride-ether complex, or mixture thereof, and the obtained condensation product is oxidized after subjecting it, if need be, to a hydrolytic treatment to thereby obtain the object material. (See Japanese Pat. Pub. Nos. 17513/1964, 17514/1964 and 3967/1971). However, each of these methods is poor in yield in the condensation step, so that the yield of the object quinone compound is very low: about 30% at the highest even in the case of crude products. Further, each of the acid catalysts used in these methods has strong corrosiveness and is liable to have a deleterious effect on the apparatus. Also, the eluted metal could contaminate the products. Thus, these methods have handicaps for industrial applications.

Moreover, the use of said type of catalysts necessitates the operations for neutralization and extraction in separating the object material from the obtained reaction products, and further, the material is wasted in great quantity in comparison with the amount of catalyst which is used at a high rate to the starting material. This is undesirable from the viewpoints of cost and pollution. Thus, each of the heretofore used methods for synthesis of the quinone compounds of the type contemplated has many difficult problems for industrial application.

Various attempts have been made for improving the yield in the condensation process, and there has been developed a method for producing the desired benzoquinone products at a high yield by combining 2,3-dimethoxy-5-methyl-6-halogeno-1,4-benzohydroquinone-1,4-dimethoxymethylether or 1,4-diacetate with a π-allyl type nickel complex expressed by the following formula (III):

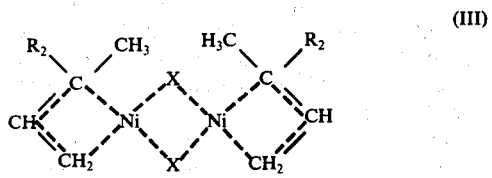

(where X stands for halogen, $R_2$ is defined above, and the site - - - - indicates half-bonding while the site ≡≡≡≡ indicates double-bonding). (Japanese Pat. Pub. Nos. 25137/1972 and 85546/1973). However, this method, although capable of significantly improving the condensation yield, still has the problem that $Ni(CO)_4$ used in adjusting the π-allyl type nickel complex (III) is virulent to the respiratory system, and also as such substance is gaseous, its treatment is difficult and troublesome for the industrial application.

With a view to working out a method capable of efficiently obtaining the quinone compounds expressed by the chemical formula (II), the present inventors have strived for improvement of the condensation process for efficiently and industrially obtaining the hydroquinone compounds which are the precursors of the quinone compounds which are the end products, and have reached the method of the present invention.

SUMMARY OF THE INVENTION

Briefly the present invention provides a method for obtaining 1,4-benzohydroquinone derivatives expressed by the chemical formula (I) by reacting 2,3-dimethoxy-6-methyl-1,4-benzohydroquinone expressed by the following formula (IV):

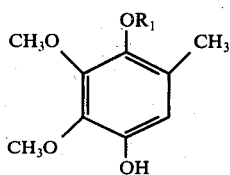

(IV)

(where R₁ stands for hydrogen or an acyl group) or monoacyl thereof with prenol or a derivative thereof (V) having the following general formula:

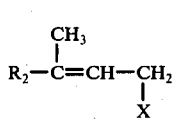

(V)

or isoprenol or a derivative thereof having the following general formula:

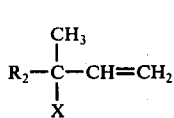

(VI)

wherein X is hydroxy group, a lower alkoxy group, an acyloxy group or a halogen atom, $R_2$ is defined as above, in the presence of an acidic catalyst for condensation which is adsorbed on an adsorbent.

As examples of (iso)prenol or its reactive derivatives to be used in the present invention, there may be cited the following: 3-methylbutene-2-ol-1, 3-methylbutene-1-ol-3, geraniol, linalol, nerol, nerolidol, farnesol, phytol, geranyl, geraniol, geranyl linalol, geranyl farnesol, geranyl nerolidol, farnecyl farnesol, farnecyl nerolidol, geranyl-geranylfarnesol, solanesol, decaprenol, isodecaprenol, undecaprenol, dodecanol, and halides or lower alkyletheresters derived from said alcohols.

The adsorbents used in practicing the method of the present invention may be those which are normally employed for chemical operations, such as silicic acid, silica gel, clay, kaolin, magnesium silicate (phloridzin), activated charcoal, permutite, natural or synthetic zeolite, alumina, silica alumina and silica magnesia.

In the method of the present invention, it is possible to use any known condensation catalyst provided that it exhibits acidity and no adsorbed component elutes out in the reaction system regardless of the method of adjustment employed. Desired adjustment can be accomplished by using any known method such as deposition method, co-precipitation method, blending method or immersion method, and if need be, firing may be performed to effect development and fixing of acidity.

As such catalysts, there can be employed a protonic acid such as formic acid, sulfuric acid, hydrochloric acid, phosphoric acid and p-toluenesulfonic acid, a Lewis acid such as zinc chloride, aluminum chloride and boron trifluoride-ether complex, and mixture thereof.

The reaction in the method of the present invention may be practiced in a liquid phase either in the presence of a solvent or without using any solvent, but use of a solvent promotes smooth progress of the reaction and also proves beneficial to the after-treatment.

In the case of using a solvent or solvents, it is important to select such type of solvents which have little possibility of causing the acid condensation catalyst to elute out from the adsorbent in which said catalyst is adsorbed. For this reason, it is preferred to use a solvent or solvents with low polarity, for example aromatic hydrocarbons such as benzene, toluene or xylene, or aliphatic hydrocarbons such as pentane, hexane, peptane, octane, isooctane, petroleum ether or ribuloine, either singly or in suitable combinations.

The method of the present invention has greatly improved the condensation step, and this has resulted in the enhanced yield of the quinone compounds (II). For instance, in the case of 2,3-dimethoxy-5-decaprenyl-6-methyl-1,4-benzoquinone (coenzyme $Q_{10}$), pure products could be obtained at a yield of 30 to 50% or even higher. Also since the acidic condensation agent does not elute out from the adsorbent, there is no fear of corroding the apparatus or contaminating the object products.

The process according to the present invention can be accomplished by either a continuous mode or batchwise mode. In the case of carrying out the process in a continuous mode, it may for instance be accomplished by first charging a reaction tower with an adsorbent in which the acidic condensation agent is adsorbed, and then passing therethrough successively or at one time (after admixing) the solution obtained by dissolving the compounds (IV) and (V) or (VI) in a solvent of the type usable in the present invention. For batch-wise practice, the process of the present invention may, for instance, be conducted by placing an adsorbent adsorbed with an acidic condensation agent in a reactor, then adding thereto the solution obtained by dissolving the compounds (IV) and (V) or (VI) in a solvent used in the present invention and agitating the mixture.

The method of the present invention can be carried out at a wide temperature range spanning from −20° to 60° C. This is a prominent advantage over the conventional methods. For instance, in the case of using a boron trifluoride - ether complex singly in the conventional methods, the reaction must be carried out within the temperature range of from room temperature to 30° C as any higher reaction temperature causes a side reaction such as formation of chroman rings or isomerization of side chains, resulting in reduced purity and yield of the end product. It is therefore necessary to perform the reaction operation for a relatively long period of time by using a low reaction temperature at which the reaction proceeds at a low speed. (see Japanese Pat. Pub. No. 3967/1971). According to the method of the present invention, however, in the case of using for instance a boron trifluoride - ether complex and silica alumina combination as catalyst, there is little possibility that any side reaction will occur even at a high temperature such as around 50° C, and hence the reaction time is also noticeably shortened.

As appreciated from the foregoing description, the present invention provides a method which, as compared with the conventional methods, can produce the compounds (I) by condensing the compounds (IV) and (V) or (VI) at a high yield and on an industrial scale. This method also allows preparation of the pharmaceutically useful quinone compounds expressed by the chemical formula (II).

The present invention is now described in detail by way of examples. In the following examples, there are shown the yields and production obtained under the same reaction conditions except for the controls wherein no adsorbent was used. Since the compounds (I) per se are extremely unstable, their production and yield were determined by measuring the compounds (II) which are oxidates of the compounds (I).

EXAMPLE 1

Preparation of 2,3-dimethoxy-5-methyl-6-nonaprenyl-1,4-benzoquinone 35 ml of benzene was added to 5 gr of zinc chloride and 18 gr of silica alumina N633H (produced by Nikki Chemicals), and the mixture was well agitated and mixed up at 50° C. Then there was further added thereto and mixed therein 11 gr of 2,3-dimethoxy-5-methyl-1,4-benzohydroquinone. Then a solution obtained by dissolving 12.6 gr of solanesol in 20 ml of benzene was added dropwise to said mixture under agitation and in a nitrogen atmosphere for 30 minutes. The reaction was continued for 30 minutes under the same conditions. The reaction mixture was filtered and the filtrate was washed with water and 5% aqueous solution of sodium hydroxide successively. After drying with Glauber's salt, the solvent was distilled off under reduced pressure. The obtained yellow oily substance was dissolved in 100 ml of ethylether, followed by addition of 2.5 gr of zinc oxide, and the mixture was agitated overnight. The reaction mixture was filtered and the filtrate was washed with water. After drying with Glauber's salt, the solvent was distilled off to obtain 14.6 gr of crude 2,3-dimethoxy-5-methyl-6-nonaprenyl-1,4-benzoquinone. This was refined by silica gel column chromatography. (Eluting solvent: 5% ethylether and hexane mixture). The eluted portion was concentrated under reduced pressure to obtain 8.9 gr of oily material. This material was crystallized from acetone to obtain orange-yellow crystals. Production: 8.4 gr (yield: 52.9%). Melting point: 45° C. Ultraviolet portion adsorption spectrum measurement: 270 mp (n-hexane). The results of measurements by infrared portion adsorption spectrum, nuclear magnetic resonance spectrum and mass spectrum agreed with the preparations.

Comparison with control

|  | Production (g) | Yield (%) | Tint |
| --- | --- | --- | --- |
| Present invention | 8.4 | 52.9 | Orange-yellow |
| Control | 4.6 | 29.0 | Red-orange |

EXAMPLE 2

Preparation of 2,3-dimethoxy-5-methyl-6-nonaprenyl-1,4-benzoquinone

Three grams of boron trifluoride etherate was added to the solvent formed by mixing 25 ml of benzene and 15 ml of hexane, followed by addition of 21 gr of silica-alumina N633H (mfd. by Nikki Chemicals), and the mixture was well agitated and mixed up. Further added thereto and mixed therein is 10 gr of 2,3-dimethoxy-5-methyl-1,4-benzohydroquinone. Then a solution obtained by dissolving 12.6 gr of solanesol in 20 ml of n-hexane was added thereto, and the mixture was subjected to the reaction treatment according to the process of Example 1 to obtain orange-yellow-colored crystals. Production: 8.1 gr (yield: 51.0%). Melting point: 45° C. The measured values by ultraviolet portion absorption spectrum, infrared portion adsorption spectrum, nuclear magnetic resonance spectrum and mass spectrum agreed with the preparations.

Comparison with control:

|  | Production (g) | Yield (%) | Tint |
| --- | --- | --- | --- |
| Present invention | 8.1 | 51.0 | Orange-yellow |
| Control | 0 | 0 | — |

EXAMPLE 3

Synthesis of 2,3-dimethoxy-5-methyl-6-nonaprenyl-1,4-benzoquinone

A condensation reaction was carried out after the fashion of Example 1 but by using 13 gr of 2,3-dimethoxy-5-methyl-1,4-benzohydroquinone-4-monoacetate, 12.6 gr of solanesol, 3 gr of boron trifluoride etherate as condensation catalyst, 18 gr of silica-alumina N633H (product of Nikki Chemicals) as adsorbent, and 15 ml of n-hexane as reaction solvent. The reaction mixture containing condensation product (monoacetate substance) was filtered to separate the adsorbent and the filtrate was washed with water and then with a weak-caustic soda aqueous solution. Then, after adding 30 ml of 30% potassium hydroxide aqueous solution, the mixture was agitated for 30 minutes at room temperature (for deacetylation). The alkali-treated material was extracted with ethylether and the ether portion was washed with water and then with saline solution, and after drying with Glauber's salt, the solvent was distilled off, obtaining 14.2 gr of oily residuum. This oily residuum (hydroquinone) was subjected to oxidation reaction and refining according to the process of Example 1, obtaining 6.7 gr of orange-yellow crystals. Yield: 42%. The results of identification measurements conducted in the same way as Example 1 agreed with the preparations.

EXAMPLE 4

Synthesis of 2,3-dimethoxy-5-methyl-6-decaprenyl-1,4-benzoquinone

Reaction treatment was carried out by following Example 3 but by using 13 gr of 2,3-dimethoxy-5-methyl-1,4-benzohydroquinone-4-monoacetate, 14 gr of isodecaprenol (synthesized from solanesol), 3 gr of boron trifluoride etherate as condensation catalyst, 18 gr of silica-alumina N633H (produced by Nikki Chemicals) as adsorbent and 20 ml of n-hexane as reaction solvent, obtaining as a result 5.1 gr of orange-yellow crystals. Yield: 33%. The identification measurements were made in the manner of Example 1, the results agreeing with the preparations.

EXAMPLE 5

Synthesis of 2,3-dimethoxy-5-methyl-6-decaprenyl-1,4-benzoquinone

Five grams of zinc chloride, 20 gr of silica alumina, 20 ml of benzene and 30 ml of n-hexane were mixed and agitated, followed by addition of 11 gr of 2,3-dimethoxy-5-methyl-1,4-benzohydroquinone, and the mixture was heated to 50° C. and agitated, and a solution prepared by dissolving 14 gr of decaprenol (purity 94%, synthesized from solanesol, trans-portion content 82%) in 10 ml of n-hexane was added dropwise to the mixture over the period of 1 hour, and thereafter, the reaction was allowed to progress for one hour under the same conditions. Upon completion of the reaction, the reaction mixture was filtered to separate the adsorbent and the filtrate was subjected to oxidation reaction and refining treatment after the mode of Example 1, obtaining 7.8 gr of orange-yellow crystals. Melting point: 49° C. Yield: 48%. The results of identification measurements conducted after the manner of Example 1 agreed with the preparations.

EXAMPLE 6

Synthesis of 2,3-dimethoxy-5-methyl-6-decaprenyl-1,4-benzoquinone

The reaction treatment was carried out after the fashion of Example 5 but by using 5 gr of zinc chloride, 20 gr of silica alumina, 20 ml of benzene, 30 ml of n-hexane, 11 gr of 2,3-dimethoxy-5-methyl-1,4-benzohydroquinone and 14 gr of isodecaprenol (purity 90%, synthesized from solanesol), obtaining 5.6 gr of orange-yellow crystals. Melting point: 49° C. Yield: 36%. The identification measurements conducted after the manner of Example 1 ensured identity with the preparations.

EXAMPLE 7

Synthesis of 2,3-dimethoxy-5-methyl-6-nonaprenyl-1,4-benzoquinone 5 gr of zinc chloride, 10 gr of Wakogel C-200 (product of Wako Junyaku), 20 ml of benzene, 30 ml of n-hexane, 12 gr of 2,3-dimethoxy-5-methyl-1,4-benzohydroquinone and 12.6 gr of pure solanesol were subjected to the reaction treatment according to the process of Example 5, obtaining 9.2 gr of orange-yellow crystals. Melting point: 45° C. Yield: 58%. The identification measurements conducted the same way as Example 1 confirmed identity with the authentic samples.

EXAMPLE 8

Synthesis of 2,3-dimethoxy-5-methyl-6-undecaprenyl-1,4-benzoquinone and 2,3-dimethoxy-5-methyl-6-dodecaprenyl-1,4-benzoquinone mixture The reaction treatment of Example 1 was carried out by using, instead of solanesol, 14 gr of the undecaprenol and dodecaprenol mixture obtained by refining dry silkwoam excrement according to the method of Japanese Pat. Pub. No. 28572/1970. There was obtained 7.2 gr of yellow oily substance.

EXAMPLE 9

25 ml of benzene and 15 ml of n-hexane were added to 4 gr of zinc chloride and 18 gr of Wakogel C-200 (product of Wako Junyaku), followed by addition of 12 gr of 2,3-dimethoxy-5-methyl-1,4-benzohydroquinone to the agitated mixture, and then a solution obtained by dissolving 10.8 gr of 90% purity isophytol in 20 ml of hexane was added dropwise to the agitated mixture for 30 minutes at 60° C, and after 30-minute reaction at the same temperature, the mixture was subjected to the same treatment as Example 1 to obtain 16.2 gr of crude 2,3-dimethoxy-5-methyl-6-phythy-1,4-benzoquinone. This was refined by silica gel chromatography to obtain 14.1 gr of pure 2,3-dimethoxy-5-methyl-6-phytyl-1,4-benzoquinone in a red-colored oily form that provides a single spot in thin-layer chromatography. Yield: 94%. The results of identification measurements conducted after the manner of Example 1 identified the preparations.

EXAMPLE 10

20 ml of benzene and 20 ml of n-hexane were added to 5 gr of zinc chloride and 15 gr silica alumina, and the mixture, while agitated, was further added with 1.5 gr of 2,3-dimethoxy-5-methyl 1,4-benzohydroquinone and heated to 60° C. Then a solution prepared by dissolving 5.7 gr of 90% purity 2,3-methylbutene-1-ol-3 in 20 ml of hexane was added dropwise to the mixture, continuing the reaction for 30 minutes at the same temperature. Then the mixture was subjected to the reaction operation of Example 1 to obtain 15.3 gr of crude 2,3-dimethoxy-5-methyl-6-pulenyl 1,4-benzoquinone. This was refined by silica gel chromatographic treatment to obtain 13.6 gr of pure 2,3-dimethoxy-5-methyl-6-pulenyl 1,4-benzoquinone in the form of a red-colored oily substance that provides a single spot in thin-layer chromatograph. Yield: 92%. The identification measurements were conducted after the pattern of Example 1 to identify the preparations.

The embodiments of the invention in which an exclusive property or privilege is claimed are defined as follows:

1. In a process for preparing a compound having the formula

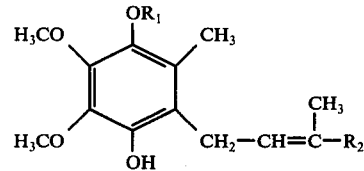

wherein $R_1$ is hydrogen or acetyl, and $R_2$ has the formula

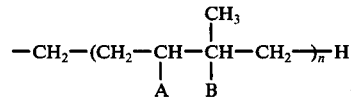

wherein n is zero or an integer from 1 to 11, A and B are hydrogen or together form a valence bond to form a double bond between the two carbon atoms to which A and B are attached, by reacting a first reactant having the formula

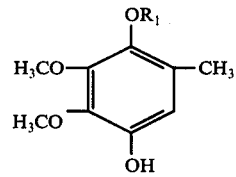

wherein $R_1$ is as defined above, with a second reactant selected from the group consisting of 3-methylbutene-2-ol-1, 3-methylbutene-1-ol-3, geraniol, linalol, nerol, nerolidol, farnesol, phytol, geranyl geraniol, geranyl linalol, geranyl farnesol, geranyl nerolidol, farnecyl farnesol, farnecyl nerolido, geranyl gernylfarnesol, solanesol, decaprenol, isodecaprenol, undecaprenol, dodecanol, and halides, lower alkyl ethers and lower alkane carboxylic acid esters thereof, the improvement which comprises the steps of: placing in a reaction zone a catalyst composition consisting essentially of a catalyst component adsorbed in an adsorbent, said catalyst component being selected from the group consisting of formic acid, sulfuric acid, hydrochloric acid, phosphoric acid, p-toluenesulfonic acid, zinc chloride, aluminum chloride, boron trifluoride-ether complex and mixtures thereof, said adsorbent being selected from the group consisting of silicic acid, silica gel, clay, kaolin, magnesium silicate, activated charcoal, permutite, natural or synthetic zeolite, alumina, silica alumina and silica magnesia; and then adding said reactants to the reaction zone and contacting same with said catalyst composition therein whereby to effect the reaction.

2. A process as claimed in claim 1, wherein the reaction is carried out at a temperature of from $-20°$ to $60°$ C.

3. A process as claimed in claim 1 in which the reaction is carried out in the presence of an inert hydrocarbon solvent.

4. A process as claimed in claim 1 including the step of filtering the reaction mixture to remove the catalyst composition and then recovering said compound from the filtrate.

* * * * *